(12) United States Patent  
Burov et al.

(10) Patent No.: US 9,131,730 B2
(45) Date of Patent: Sep. 15, 2015

(54) SYSTEM AND APPARATUS FOR REGISTRATION OF DIFFERENT OBJECTS IN ROD SHAPED ARTICLES

(75) Inventors: Todor Burov, Plovdiv (BG); Dimitar Yanchev, Plovdiv (BG)

(73) Assignee: AIGER GROUP AG, Zug (CH)

( * ) Notice: Subject to any disclaimer, the term of this patent is extended or adjusted under 35 U.S.C. 154(b) by 1195 days.

(21) Appl. No.: 12/683,918

(22) Filed: Jan. 7, 2010

(65) Prior Publication Data

US 2011/0162665 A1 Jul. 7, 2011

(51) Int. Cl.
| | |
|---|---|
| A24C 1/14 | (2006.01) |
| A24C 1/44 | (2006.01) |
| A24C 5/33 | (2006.01) |
| A24C 5/34 | (2006.01) |
| A24D 3/02 | (2006.01) |
| G01N 21/952 | (2006.01) |

(52) U.S. Cl.
CPC ............ *A24C 5/3412* (2013.01); *A24D 3/0295* (2013.01); *G01N 21/952* (2013.01)

(58) Field of Classification Search
None
See application file for complete search history.

(56) References Cited

U.S. PATENT DOCUMENTS

| | | |
|---|---|---|
| 3,297,038 A | 1/1967 | Homburger |
| 3,308,600 A | 3/1967 | Erdmann et al. |
| 3,339,557 A | 9/1967 | Karalus |
| 3,339,558 A | 9/1967 | Waterbury |
| 3,366,121 A | 1/1968 | Carty |
| 3,390,686 A | 7/1968 | Irby, Jr. et al. |
| 3,420,242 A | 1/1969 | Boukair |
| 3,424,172 A | 1/1969 | Neurath et al. |
| 3,428,049 A | 2/1969 | Leake et al. |
| 3,508,558 A | 4/1970 | Seyburn |
| 3,513,859 A | 5/1970 | Carty |
| 3,547,130 A | 12/1970 | Harlow et al. |
| 3,550,750 A | 12/1970 | Jackson |
| 3,575,180 A | 4/1971 | Carty |
| 3,596,665 A | 8/1971 | Lindgard |
| 3,602,231 A | 8/1971 | Dock |
| 3,625,228 A | 12/1971 | Dock |

(Continued)

FOREIGN PATENT DOCUMENTS

| | | |
|---|---|---|
| EA | 005284 B1 | 12/2004 |
| EP | 0500300 A2 | 8/1992 |

(Continued)

OTHER PUBLICATIONS

International Search Report and Written Opinion dated Oct. 18, 2012, as issued in corresponding International Application No. PCT/IB 2011/000165 filed Jan. 5, 2011.

*Primary Examiner* — Richard Crispino
*Assistant Examiner* — Phu Nguyen
(74) *Attorney, Agent, or Firm* — Maier & Maier, PLLC

(57) ABSTRACT

A method, system and apparatus for registering different objects in filter rod shaped articles, for example as found in the tobacco processing industry. The method, system and apparatus can include a rod containing cigarette filter components; one or more sensors that determine the constitution of segments of the rod and transmits one or more signals regarding segments of the rod; a processor that receives the one or more signals from the one or more sensors, performs a comparison between the one or more signals and known data and transmits a signal based upon results of the comparison; and an ejector that receives the signal from the processor and removes any segment of the rod that does not conform with the known data.

11 Claims, 3 Drawing Sheets

(56) References Cited

U.S. PATENT DOCUMENTS

| | | | |
|---|---|---|---|
| 3,635,226 A | 1/1972 | Horsewell et al. | |
| 3,669,128 A | 6/1972 | Cohen | |
| 3,685,521 A | 8/1972 | Dock | |
| 3,797,644 A | 3/1974 | Shaw | |
| 3,818,223 A | 6/1974 | Gibson et al. | |
| 3,915,176 A | 10/1975 | Heitmann et al. | |
| 3,916,914 A | 11/1975 | Brooks et al. | |
| 3,972,335 A | 8/1976 | Tiggelbeck et al. | |
| 3,991,773 A | 11/1976 | Walker | |
| 3,993,194 A * | 11/1976 | Reuland | 209/535 |
| 4,003,387 A | 1/1977 | Goldstein | |
| 4,033,387 A | 7/1977 | Nijs et al. | |
| 4,046,153 A | 9/1977 | Kaye | |
| 4,082,098 A | 4/1978 | Owens, Jr. | |
| 4,126,141 A | 11/1978 | Grossman | |
| 4,238,993 A | 12/1980 | Brand et al. | |
| 4,280,187 A | 7/1981 | Reuland et al. | |
| 4,281,670 A | 8/1981 | Heitmann et al. | |
| 4,281,671 A | 8/1981 | Bynre et al. | |
| 4,284,088 A | 8/1981 | Brand et al. | |
| 4,291,713 A | 9/1981 | Frank | |
| 4,474,190 A | 10/1984 | Brand | |
| 4,574,816 A | 3/1986 | Rudszinat | |
| 4,677,995 A | 7/1987 | Kallianos et al. | |
| 4,723,559 A | 2/1988 | Labbe | |
| 4,729,391 A | 3/1988 | Woods et al. | |
| 4,736,754 A | 4/1988 | Heitmann et al. | |
| 4,781,203 A | 11/1988 | La Hue | |
| 4,807,809 A | 2/1989 | Pryor et al. | |
| 4,811,745 A | 3/1989 | Cohen et al. | |
| 4,844,100 A | 7/1989 | Holznagel | |
| 4,848,375 A | 7/1989 | Patron et al. | |
| 4,850,301 A | 7/1989 | Greene, Jr. et al. | |
| 4,862,905 A | 9/1989 | Green, Jr. et al. | |
| 4,865,056 A | 9/1989 | Tamaoki et al. | |
| 4,878,506 A | 11/1989 | Pinck et al. | |
| 4,889,144 A | 12/1989 | Tateno et al. | |
| 4,925,602 A | 5/1990 | Hill et al. | |
| 4,941,486 A | 7/1990 | Dube et al. | |
| 5,012,823 A | 5/1991 | Keritsis et al. | |
| 5,012,829 A | 5/1991 | Thesing et al. | |
| 5,025,814 A | 6/1991 | Raker | |
| 5,060,664 A | 10/1991 | Siems et al. | |
| 5,060,665 A | 10/1991 | Heitmann | |
| 5,156,169 A | 10/1992 | Holmes et al. | |
| 5,191,906 A | 3/1993 | Myracle et al. | |
| 5,220,930 A | 6/1993 | Gentry | |
| 5,223,185 A | 6/1993 | Takei et al. | |
| 5,225,277 A | 7/1993 | Takegawa et al. | |
| 5,271,419 A | 12/1993 | Arzonico et al. | |
| 5,331,981 A | 7/1994 | Tamaoki et al. | |
| 5,387,093 A | 2/1995 | Takei | |
| 5,387,285 A | 2/1995 | Rivers | |
| 5,476,108 A | 12/1995 | Dominguez et al. | |
| 5,724,997 A | 3/1998 | Smith et al. | |
| 6,229,115 B1 | 5/2001 | Voss et al. | |
| 6,360,751 B1 | 3/2002 | Fagg et al. | |
| 6,384,359 B1 | 5/2002 | Belcastro et al. | |
| 6,385,333 B1 | 5/2002 | Puckett et al. | |
| 6,647,870 B2 | 11/2003 | Kohno | |
| 6,779,530 B2 | 8/2004 | Kraker | |
| 6,848,449 B2 | 2/2005 | Kitao et al. | |
| 6,904,917 B2 | 6/2005 | Kitao et al. | |
| 7,074,170 B2 | 7/2006 | Lanier, Jr. et al. | |
| 7,115,085 B2 | 10/2006 | Deal | |
| 8,186,359 B2 | 5/2012 | Ademe et al. | |
| 2001/0012331 A1 * | 8/2001 | Conrads et al. | 378/98.7 |
| 2002/0020420 A1 | 2/2002 | Xue et al. | |
| 2002/0166563 A1 | 11/2002 | Jupe et al. | |
| 2003/0098033 A1 | 5/2003 | Macadam et al. | |
| 2003/0136419 A1 | 7/2003 | Muller | |
| 2003/0145866 A1 | 8/2003 | Hartmann | |
| 2003/0178036 A1 | 9/2003 | Demmer et al. | |
| 2004/0129281 A1 | 7/2004 | Hancock et al. | |
| 2004/0261807 A1 | 12/2004 | Dube et al. | |
| 2005/0016556 A1 | 1/2005 | Ashcraft et al. | |
| 2005/0039764 A1 | 2/2005 | Barnes et al. | |
| 2005/0054501 A1 * | 3/2005 | Schroder | 493/39 |
| 2005/0066986 A1 | 3/2005 | Nestor et al. | |
| 2005/0070409 A1 | 3/2005 | Deal | |
| 2005/0076929 A1 | 4/2005 | Fitzgerald et al. | |
| 2005/0103355 A1 | 5/2005 | Holmes | |
| 2005/0133051 A1 | 6/2005 | Luan et al. | |
| 2005/0194014 A1 | 9/2005 | Read, Jr. | |
| 2006/0112964 A1 | 6/2006 | Jupe et al. | |
| 2006/0144412 A1 | 7/2006 | Mishra et al. | |
| 2006/0174901 A1 | 8/2006 | Karles et al. | |
| 2006/0207616 A1 | 9/2006 | Hapke et al. | |
| 2006/0272655 A1 | 12/2006 | Thomas et al. | |
| 2006/0272663 A1 | 12/2006 | Dube et al. | |
| 2006/0293157 A1 | 12/2006 | Deal | |
| 2007/0012327 A1 | 1/2007 | Karles et al. | |
| 2007/0068540 A1 | 3/2007 | Thomas et al. | |
| 2007/0095357 A1 | 5/2007 | Besso et al. | |
| 2007/0117700 A1 | 5/2007 | Kushihashi et al. | |
| 2007/0246055 A1 | 10/2007 | Oglesby | |
| 2008/0029118 A1 | 2/2008 | Nelson et al. | |
| 2009/0090372 A1 | 4/2009 | Thomas et al. | |
| 2009/0120449 A1 | 5/2009 | Tindall | |
| 2009/0145449 A1 | 6/2009 | Cieslikowski et al. | |
| 2010/0099543 A1 | 4/2010 | Deal | |

FOREIGN PATENT DOCUMENTS

| | | |
|---|---|---|
| EP | 1702524 A1 | 9/2006 |
| EP | 1767107 A1 | 3/2007 |
| GB | 709203 | 5/1954 |
| GB | 737329 | 9/1955 |
| GB | 778044 | 7/1957 |
| GB | 807404 | 1/1959 |
| SU | 272925 A3 | 9/1970 |
| WO | WO 03/009711 A1 | 2/2003 |
| WO | WO 03/055338 A2 | 7/2003 |
| WO | WO 2004/047572 A1 | 6/2004 |
| WO | WO 2004/057986 A2 | 7/2004 |
| WO | WO 2006/064371 A1 | 6/2006 |
| WO | WO 2006/136196 A1 | 12/2006 |
| WO | WO 2006/136197 A1 | 12/2006 |
| WO | WO 2006/136198 A1 | 12/2006 |
| WO | WO 2006/136199 A1 | 12/2006 |
| WO | WO 2007/010407 A3 | 1/2007 |
| WO | WO 2007/012981 A2 | 2/2007 |
| WO | WO 2007/012981 A3 | 2/2007 |
| WO | WO 2007/038053 A1 | 4/2007 |
| WO | WO 2007/060543 A2 | 5/2007 |
| WO | WO 2008/012329 A2 | 1/2008 |

\* cited by examiner

SYSTEM AND APPARATUS FOR REGISTRATION OF DIFFERENT OBJECTS IN ROD SHAPED ARTICLES

BACKGROUND

Cigarettes and other smoking articles commonly include filter portions (known as filter segments) which may be used to remove some impurities and toxins from cigarette smoke as it is inhaled. To make this process more efficient, filters with several different segments have been developed in the tobacco industry—for example duo filter, triple filter and the like. The segments may differ in size, shape and construction. For example there are filter segments made of carbon, accetate, paper, tobacco and other products and items. Further, they may have any of a variety of shapes, for example conical, cylindrical, etc. Recently filters with different ingredients inside have been developed, such as breakable capsules, mini capsule and massive pieces from different chemical elements. These may be used for a variety of purposes, such as imparting flavor or reducing some chemical elements from the cigarette smoke as it is inhaled by the smoker.

As mentioned above, one method of imparting flavor to a cigarette may be to include a flavor capsule within the filter portion of a cigarette. When the capsule is ruptured, it releases flavorings or aromatic material into the air stream passing through the filter. These capsules may also alter other characteristics of the inhaled smoke, such as, for example, cooling or moistening the smoke such that the smoker is provided with an enhanced smoking experience.

Additionally, specialized cigarette filters are known to incorporate a variety of elements, for example filter segments including acetate, carbon and paper elements, as well as empty or "recess" areas. Different numbers of elements are combined in varying forms in different types of filters. Further, filter elements can include both fragment elements and solid elements. Fragment elements may be distributed throughout a filter whereas solid elements may be larger than fragment elements and may be located at disposed at predetermined locations in a filter. The location of both fragment elements and solid elements may be related to the overall quality of the filter. Current methods and systems for the construction or manufacture of filters are slow and can not meet the demands of filter construction, for example with respect to the design and variety of filters.

SUMMARY

An apparatus that registers different objects in rod shaped articles. The apparatus can include a rod containing cigarette filter components; one or more sensors that determine the constitution of segments of the rod and transmits one or more signals regarding segments of the rod; a processor that receives the one or more signals from the one or more sensors, performs a comparison between the one or more signals and known data and transmits a signal based upon results of the comparison; and an ejector that receives the signal from the processor and removes any segment of the rod that does not conform with the known data.

A method for making cigarette filters may also be described. The method can include passing a continuous filter rod through a plurality of sensors; determining the composition of segments of the continuous with the sensors; comparing the composition of the segments to predetermined data; and rejecting segments whose composition does not correlate to the predetermined data.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1:
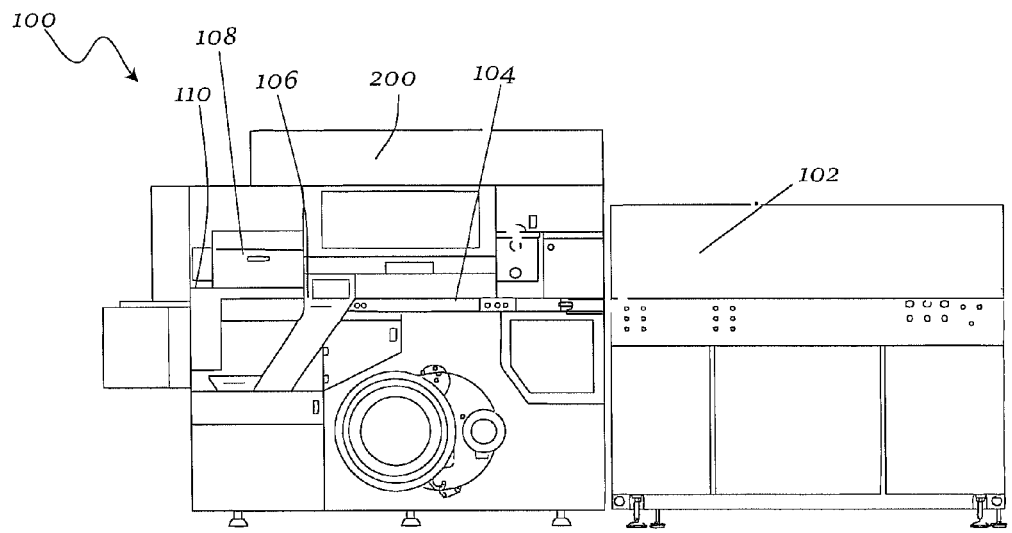
FIG. 1 is an exemplary diagram of an apparatus for producing any of a variety of types of cigarette filters.

Exemplary FIG. 1 can show a known system for producing cigarette filters 100 using a preparation machine. The machine 100 can include a preparation machine 102. The preparation machine 102 can include any number of different modules having a variety of functions. The preparation machine 102 can prepare raw materials and form them into a rod or assemble filter segments into a desired order. The terms "rod" and "filter", amongst others used herein, can be used to describe any of a variety of known rod and filter types independent of construction or stage-of-construction, for example single or multiple segment filters, carbon or paper filters and the like. Additionally, machine can put solid or any other type of objects inside a rod 104, for example, as a rod is moved through machine 102. Rod 104 may be, in some exemplary embodiments, a continuous filter rod which can further have a number of components or segments and which may be formed or cut into any number of cigarette filters. The continuous filter rod 104 may then go through sensor 106 of the registration system 200 (described in more detail below). The continuous rod 104 may then be cut by a cutting device 108 at a desired length. However, if sensor 106 detects a bad or malformed filter, for example a filter having an undesired constitution, such as one or more missing or improperly positioned objects, construction or components the registration system can reject it with ejector 110.

Figure 2:
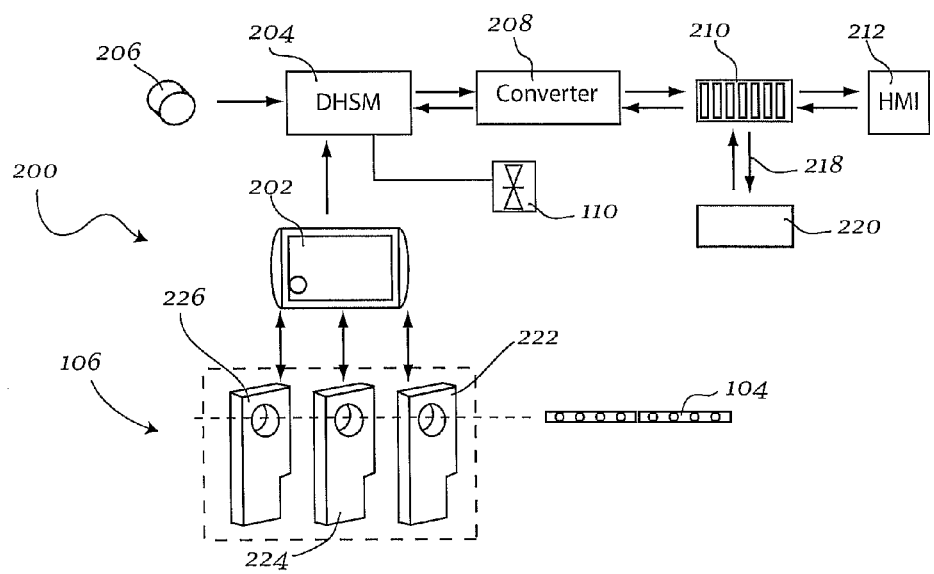
FIG. 2 is a view of an exemplary embodiment of a registration system.

Turning to exemplary FIG. 2, a modular registration system 200 may be shown and described which can have a variety of applications, while being highly flexible, reliable and precise. Registration system 200 can include any number of components, for example sensor 106 which can include one or more different types of sensors 222, 224 and 226, as described above, a junction and acceleration module 202, one or more digital high speed modules 204, encoder 206, converter 208, programmable logic controller (PLC) 210, interface 212 (which may be a human-machine interface (HMI)) and ejector 110. As described in further detail below, junction and acceleration module 202 may act to boost or increase the signal strength of any signal from sensors 222, 224 and 226 in sensor 106, digital high speed module 204 may convert signals from one form to another and make comparisons, encoder 206 may determine a time or times when one or more sensors 222-226 are active, converter 208 may convert any signals into appropriate or acceptable format for PLC 210 and PLC 210 may have a memory that can include stored data for comparisons.

Figure 3:
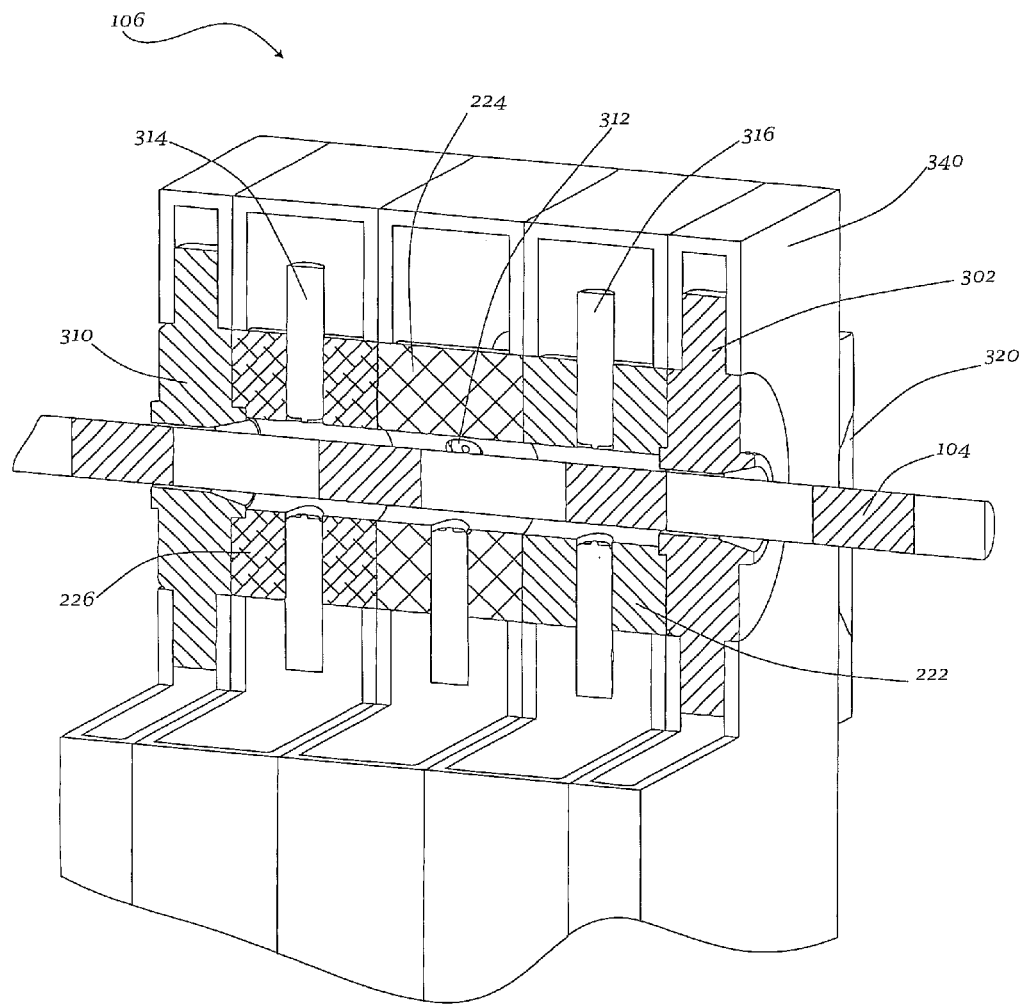
FIG. 3 is a view of an exemplary diagram showing modularity of a variety of sensors.

As further shown in exemplary FIG. 3, a more detailed diagram of sensor 106, one or more sensors may be shown. Sensor 106 may include any number of sensors, which may be plug and play modular sensors, for example modules 222, 224 and 226, as described above. Modules 222, 224 and 226 may be any type of modules, for example modules that include some form of sensing or sensory capability. As mentioned above, modules 222, 224 and 226 may further be such that they can enjoy plug and play compatibility which can allow them to be changed, replaced, swapped out or otherwise altered in a short amount of time. Any of sensors 312, 314 and 316 can be mounted in a separate standardized module 222, 224 and 226, in some further exemplary embodiments. For example any single module or any number of modules 302 through 310 or 222 through 226 may be removed and replaced quickly and easily, for example through a utilization of quick release device 320. Quick release device 320 may allow for fast and precise mounting of any sensors with respect to rod 104. Further, depending on different types of filters that may be desired to be made, different modules may be utilized and the plug and play compatibility of modules 222 through 226 may allow for the utilization of any desired modules within a minimal amount of time. Modules 222 through 226 can be any type of modules, for example sensory modules such as optical, laser, inductive, capacity, microwave, pneumatic, any other type of wave, video, any type of cameras or any other known type of module or sensor that can allow for the sensing of any desired property. Additionally, modules 222 through 226 may be any combination of modules, for example separate or unique types of modules for each of modules 222, 224 and 226. Any of modules 222 through 226 may then be formed into or coupled to form one or more sensors 312, 314 or 316. For example, one or more modules 222 through 226 can be coupled together in any number of orientations to form a sensor, as further described below. Additionally, other modules, for example modules 302 and 310 may be utilized or used in a similar manner. Further, each sensor or any desired number of sensors may be positioned inside a housing, for example housing 340. Housing 340 may be formed out of any desired material and may protect any components inside housing 340 from mechanical, chemical or other forms of damage or interference. In some further exemplary embodiments, housing 340 may act to seal any internal components from outside elements.

Still referring to exemplary FIG. 3, module 302 may be an entry module and may provide for an initial scanning or reading of rod 104 as it enters system 200. Further, other components may be activated upon an initial scanning or reading of rod 104 performed by module 302. Also, in some examples, a reading or scanning by module 302 may designate a leading edge of a filter segment that is to be cut from rod 104. Additionally, another module, module 310, may be an exit module. Thus, in some exemplary embodiments, a reading by module 310 may be a final reading or scan of rod 104 and may designate a trailing edge of a filter segment that is to be cut from rod 104.

Still referring to FIG. 3, some further exemplary embodiments can include cleaning nozzles 312. Cleaning nozzles 312, for example, may function by blowing clean or vacuuming clean any sensor onto which dirt or any other undesired contaminants may have accumulated. Further, any modules and sensors discussed herein may work together or otherwise in conjunction to provide sensory results with a high degree of accuracy. Further, additional sensors, for example sensors 314, may be placed or otherwise oriented inside sensor 314, for example as shown in exemplary FIGS. 4a and 4b.

Figure 4A:
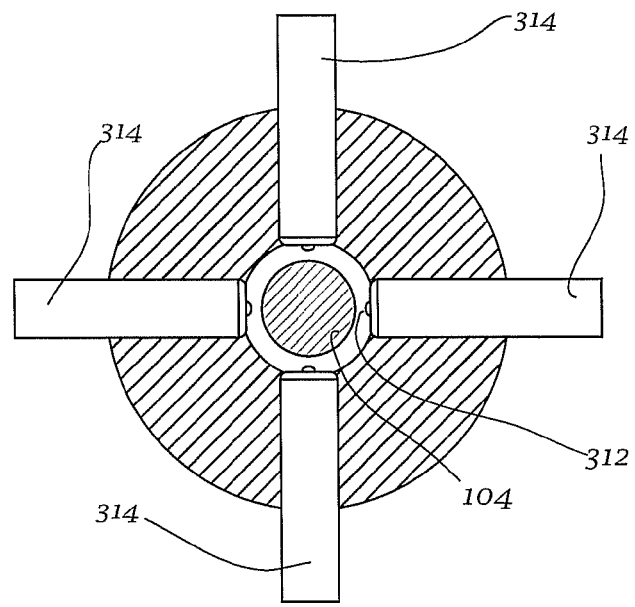
FIG. 4a is an exemplary diagram showing an embodiment of a sensor.
Figure 4B:
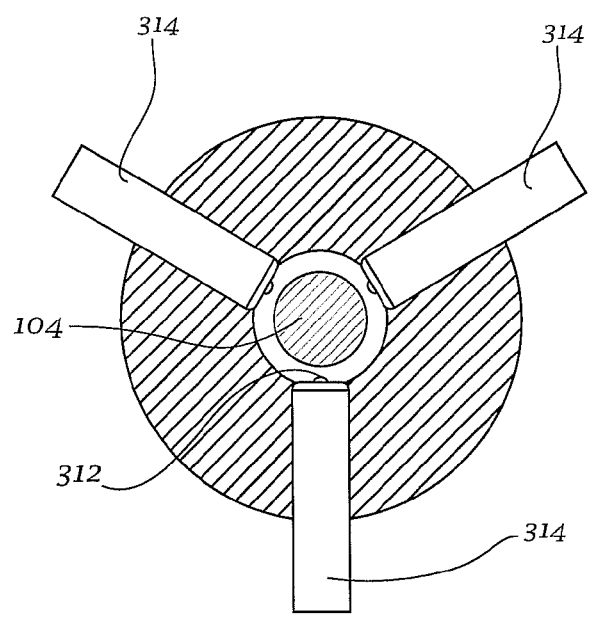
FIG. 4b is an exemplary diagram showing another embodiment of a sensor.

In exemplary FIG. 4a, an exemplary sensor orientation may be shown. Here, four sensors 314 may be mounted at approximately 90 degree angles from each other and may be disposed about rod 104 as it passed through system 200. Additionally, each of sensors 314 may include cleaning nozzles 312 as described above. In another exemplary embodiment, as shown in FIG. 4b, three sensors 314 may be mounted at approximately 120 degree angles from each other and may be disposed about rod 104 as it passed through system 200. Similarly, each of sensors 314 may include cleaning nozzles 312 as described previously. In further exemplary embodiments, sensors 314 may be mounted, disposed or coupled in any desire and may be able to scan rod 104 in any manner, for example a 360 degree scan.

Referring back to exemplary FIG. 3, in one exemplary embodiment, each sensor, for examples the one or more sensors in modules 302 through 310, may have a different or unique application. For example, module 222 may have a laser detector which may allow it determine the location of a capsule which may be disposed in a filter segment to be cut from rod 104. Further, module 224 may have a microwave sensor which can determine a capsule position or broken capsule or capsule fragments in the constitution of a filter which may be disposed in a filter segment to be cut from rod 104. Additionally, module 226 can have a capacity sensor, which may determine the humidity of a segment of rod 104 and the quantity of any different substances used to form a segment of rod 104. Further, module 224 may have a video camera that provides a video signal, which may allow for the determination, either in a machine readable manner or human readable manner, of any visual defects or geometrical differences that might occur during production. Each module or any number of modules may work in parallel to provide any data collected thereby to junction and acceleration module 202, as shown in exemplary FIG. 2.

Junction and acceleration module 202 may help regulate or control signals from any of modules 302 through 310 as well as any plug and play sensors. Different numbers and type of modules can be attached to the said junction and acceleration module 202. For example, junction and acceleration module 202 may boost or accelerate a signal from any sensors, allowing for a relatively low or weak signal or signals to become a more robust, higher signal or signals, or otherwise a signal or signals with greater strength. Any signals may then be sent from the junction and acceleration module 202 to digital high speed module 204. Digital high speed module 204 may digitize any signals sent thereto, for example converting them from analog to digital if desired. Digital high speed module 204 may further have any desired number of inputs allow it to receive any number of signals from any number of transmitting sensors or modules, such as modules 302 through 310 or junction and acceleration module 202, at any time. In some exemplary embodiments, it may also be desired to have a number of digital high speed modules that may be connected together. Such a grouping of digital high speed modules may in order to increase the capacity of the system 200 insofar as more sensors may be added, for example, in a plug and play manner.

In a further exemplary embodiment, any number of sensors, such as sensors 314, of a same or similar type may be disposed in system 200. For example, a higher number of sensors 314 in system 200 may allow for the generation and compilation of a larger amount of signal data which may then be analyzed faster, for example simultaneously analyzing and processing the signals which may allow for higher precision. Further, in some exemplary embodiments, digital high speed module 204 can also include a processor or processing capabilities that may allow it to compare any signals which may be inputted into digital high speed module 204. Further, digital high speed module 204 can compare any inputted signals from any sensors, such as sensors 314 to a known or predetermined signal or pattern. The known signal or pattern may be a signal generated from or a pattern of a known type or brand of cigarette filter and which may be stored in PLC 210, as described below. Further, the known signal or pattern may be of a filter that is fulfills a predetermined or desired constitution, construction, composition or quality criteria. Following any comparison made by digital high speed module 204 of incoming signals against a known signal or pattern, an output may be produced. The output may indicate that a filter segment whose composition, construction, geometrical shape, quality criteria or any is appropriate or desired, resulting in a "good" output or signal otherwise indicating that the filter segment is acceptable and the filter segment may continue through any further components of machine 100. However, in situations where the filter segment does not comply with a desired construction, composition or any quality criteria indicated by the known signal or pattern, a "bad" output or signal otherwise indicating the filter segment is bad. The filter segment may then be removed by ejector 110, for example after it is cut by cutting device 108.

Known signals or patterns can be stored in a memory, for example a memory associated with PLC 210. The memory in PLC 210 may be referred to as a brand manager. The brand manager in PLC 210 may store known signals or patterns that have the desired parameters for filters or filter segments, such as those described previously. Further, data provided by digital high speed module 204 may be converted into a desired format by converter 208 so that it may be compared to the stored data in PLC 210.

The desired parameters for filters stored in PLC 210 can include the best or most demanded parameters for each or any sensor. While known signals or parameters may be stored on PLC 210 in any desired manner, an interface, such as human machine interface (HMI) 212 may be utilized or otherwise associated with PLC 210. HMI 212 may allow for a computer operator to enter any desired data, such as known signals or patters, add, edit or change any desired data. System 200 may also, in some exemplary embodiments, include a self learning mode which can act to improve or otherwise optimize any sensor performance parameters during otherwise routine operation. Further, any new or additional known signals or patterns or other parameters may also inputted into system 200 through HMI 212 through the use of physical products and a sensory examination thereof. Also, as system 200 is working to produce products, a mathematical model of the sensitivity and working parameters of the sensors may be adjusted either automatically or manually through HMI 212 as desired, for example in real time. Additionally, various settings and pre-sets of any programmable sensors can be stored, for example, in a "sensor library" of the PLC 210.

When any type of filter is chosen from the brand manager, the PLC 210 can send hardware settings to an appropriate sensor (for example sensor 314). Thus the sensor may be automatically programmed or set-up for an appropriate type of filter being produced.

In some further exemplary embodiments, PLC 210 may also record, tabulate and/or store any statistical data regarding products of system 200, for example filter segments. Exemplary data can include the number of "good" filter segments compared to the number of "bad" filter segments. Additionally, as described previously, upon the receipt of a "bad" signal, digital high speed module 204 may send a signal to ejector 110 which can act to remove the undesired filter segment from system 200 without any interruption of or effect on further production.

In another exemplary embodiment, the components of system 200 may be synchronized. For example, encoder 206 may act to determine when any sensors, for examples sensors in modules 302 through 310, perform a measurement or otherwise perform a sensing action. The encoder 206 may make these determinations and then synchronize the sensors with the speed of rod 104 of system 200.

In yet a further exemplary embodiment, system 200 may synchronize any data received from any sensors with the cutting device 108, which may be a cutting head device. Cutting device 108 may function to cut rod 104 at any desired interval or intervals. For example, cutting device 108 may cut rod 104 at precisely determined intervals so as to form filters having a desired length. Additionally cutting device 108 may cut rod 104 at desired or precise intervals so as to maintain a desired distance between a filter segment and/or capsule in a filter from a beginning of a filter.

In still further exemplary embodiments, system 200 may be a stand alone system. Therefore, as desired, system 200 may be integrated into or incorporated with any other known system so as to improve a desired manufacturing process. For example, the system 200 can be connected to another control system 220 through a standard communication interface 218. Thus the system 200 can exchange information with other systems, any networked or internet-accessible system or machine or any other hardware or software as desired.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An apparatus that registers different objects in filter rod shaped articles, comprising:
   a rod containing cigarette filter components;
   a plurality of sensors that determine the constitution of segments of the rod and transmits one or more signals regarding segments of the rod, wherein at least two of the plurality of sensors are radially disposed equidistantly about a circumference of the rod to simultaneously determine the same characteristics of the components of the rod;
   a processor programmed with a mathematical model of desired components of the rod, the processor receives and stores the one or more signals from the plurality of sensors, performs a comparison between the one or more signals and known data from the mathematical model, transmits a signal based upon results of the comparison, and automatically adjusts the mathematical model based on the stored one or more signals; and an ejector that receives the signal from the processor and removes any segment of the rod that does not conform with the known data.

2. The apparatus of claim 1, further comprising a cutting device that cuts the rod into segments at predetermined intervals.

3. The apparatus of claim 1, wherein the plurality of sensors work in parallel to provide precise determination of the characteristics of the components of the rod.

4. The apparatus of claim 1, further comprising a memory that stores the known data.

5. The apparatus of claim 1, wherein the known data is characteristics of a cigarette filter segment.

6. The apparatus of claim 1, wherein the processor further compiles data regarding the characteristics of segments of the rod and has preset programs for the plurality of sensors.

7. The apparatus of claim 1, further comprising an interface.

8. The apparatus of claim 1, further comprising one or more modules housing the plurality of sensors.

9. The apparatus of claim 1, wherein the one or more modules are removable and replaceable during common machine operation mode.

10. The apparatus of claim 1, wherein the processor further compiles data in a memory and uses the data to optimize performance of the plurality of sensors.

11. The apparatus of claim 1, wherein the plurality of sensors are comprised of microwave sensors, optical sensors, video sensors, camera sensors, laser sensors, pneumatic sensors, inductive sensors and capacity sensors.

* * * * *